United States Patent [19]
Caubere et al.

[11] Patent Number: 5,635,516
[45] Date of Patent: Jun. 3, 1997

[54] (THIA) CYCLOALKYL[B]INDOLE COMPOUNDS AS ANTI-INFLAMMATORY AGENTS

[75] Inventors: Paul Caubere, Nancy; Brigitte Jamart-Gregoire, Vandoeuvre Les Nancy; Catherine Caubere, Nancy; Dominique Manechez, Puteaux; Pierre Renard, Versailles; Gérard Adam, Le Mesnil Le Roi; Catherine Nguyen, Lingolsheim, all of France

[73] Assignee: Adir et Compagnie, Courbevoie, France

[21] Appl. No.: 495,226

[22] Filed: Jun. 27, 1995

[30] Foreign Application Priority Data

Jun. 28, 1994 [FR] France ................................ 94.07888

[51] Int. Cl.⁶ .................... A61K 31/47; A61K 31/44; C07D 215/12
[52] U.S. Cl. .................... 514/314; 514/307; 514/339; 546/148; 546/152; 546/268.1
[58] Field of Search .................... 546/148, 152, 546/272, 268.1; 514/307, 314, 339

[56] References Cited

U.S. PATENT DOCUMENTS

| | | | |
|---|---|---|---|
| 5,221,678 | 6/1993 | Atkinson | 514/311 |
| 5,280,047 | 1/1994 | Mueller | 514/678 |
| 5,288,751 | 2/1994 | Brooks | 514/438 |
| 5,420,131 | 5/1995 | Carceller | 514/253 |

OTHER PUBLICATIONS

Gallin JI, Goldstein IM, Snyderman R. "Inflammation. Basic Principles and Clinincal Correlates". Raven Press, New York. p. 1130 1992.

*Primary Examiner*—C. Warren Ivy
*Assistant Examiner*—Evelyn Huang
*Attorney, Agent, or Firm*—The Firm of Gordon W. Hueschen

[57] ABSTRACT

A compound selected from those of formula (I):

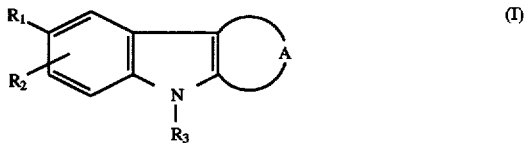

in which $R_1$, $R_2$, $R_3$ and A are as defined in the description.

11 Claims, No Drawings

(THIA) CYCLOALKYL[B]INDOLE COMPOUNDS AS ANTI-INFLAMMATORY AGENTS

The invention relates to new (thia)cycloalkyl[b]indole compounds, to a process for the preparation thereof, and to pharmaceutical compositions containing them.

There are known as prior art the compounds of Application EP 468 785, which are described as being anti-inflammatory agents, but the latter teach that substitution on the cycloalkyl moiety is always necessary.

The Applicant has found powerful anti-inflammatory compounds that do not have the side-effects (gastrointestinal toxicity) exhibited by the cyclo-oxygenase inhibitors currently on the market.

The anti-inflammatory activity of the compounds of the invention makes available to the clinician therapeutic agents that can be used for inhibiting certain processes (especially 5-lipoxygenase activation) which are involved in a number of pathologies having an anti-inflammatory component (including arthritis, colitis and psoriasis), without affecting the cyclo-oxygenase pathway.

In particular, the compounds of the invention allow inhibition of 5-lipoxygenase via an anti-FLAP mechanism ("five lipoxygenase activatory protein"), the inhibition proving to be much greater than that of redox inhibitors or of iron chelators.

The invention relates more especially to compounds of formula (I):

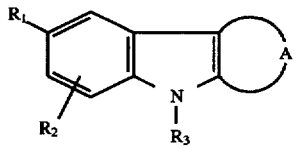

in which:

$R_1$ represents Ar—$(CH_2)_n$—O— wherein n represents zero or 1 to 4 inclusive and Ar is selected from phenyl, naphthyl, thienyl, furyl, pyrrolyl, imidazolyl, pyrazolyl, thiazolyl, isothiazolyl, oxazolyl, isoxazolyl, thiadiazolyl, oxadiazolyl, pyridyl, quinolyl, isoquinolyl, indolyl, benzofuryl and benzothienyl, Ar being unsubstituted or substituted by one or more radicals selected from halogen, alkyl, alkoxy, hydroxy and trifluoromethyl;

$R_2$ is selected from hydrogen, halogen, alkyl, alkoxy and trifluoromethyl;

$R_3$ is selected from hydrogen, alkyl, carboxyalkyl and alkoxycarbonylalkyl, and A represents —$(CH_2)_m$— wherein m is from 3 to 6, or represents a group of formula ($\alpha$):

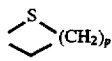

in which p is from 1 to 4;

wherein the terms "alkyl" and "alkoxy" denote linear or branched groups having from 1 to 6 carbon atoms inclusive, their optical isomers, in pure form or in the form of a mixture, and their pharmaceutically-acceptable addition salts with an acid or a base.

Of the pharmaceutically acceptable bases that can be used for converting the compounds according to the invention into salts there may be mentioned by way of non-limiting example sodium hydroxide, potassium hydroxide, triethylamine, diethylamine, ethanolamine, arginine, lysine and diethanolamine.

Of the pharmaceutically acceptable acids that can be used for converting the compounds according to the invention into salts there may be mentioned by way of non-limiting example hydrochloric acid, sulfuric acid, phosphoric acid, tartaric acid, malic acid, fumaric acid, oxalic acid, methanesulfonic acid, ethanesulfonic acid, camphoric acid and citric acid.

The invention relates also to a process for the preparation of compounds of formula (I), characterised in that the compound of formula (II):

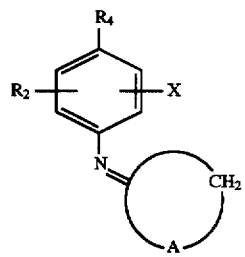

in which $R_2$ and A are as defined in formula (I), X represents a halogen atom and $R_4$ represents an alkoxy radical, or tetrahydropyranyloxy, is condensed in the presence of sodium amide or a combination thereof with an alcoholate (complex base), such as the complex base sodium amide-sodium tert.-butoxide (NaNH$_2$-tBuONa), to obtain:

either a compound of formula (III):

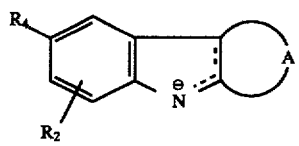

in which $R_2$, $R_4$ and A are as defined above, or, after hydrolysis, a compound of formula (IV):

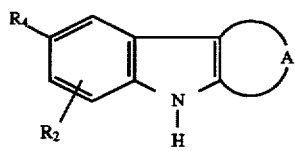

in which $R_2$, $R_4$ and A are as defined above, which compound of formula (III), or compound of formula (IV) in the form of its alkali salt, is substituted on the indole nitrogen by a radical of the formula $R_3'$, wherein $R_3'$ has the same meanings as $R_3$ in the definition of formula (I) with the exception of hydrogen, to obtain a compound of formula (V):

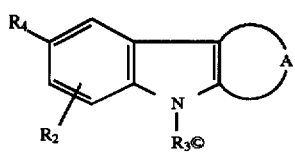

in which $R_2$, $R_4$, A and $R_3'$ are as defined above, which compound of formula (IV) or (V) is subjected to dealkylation, for example is subjected to the action of a mixture of formula (VI):

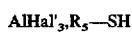

in which Hal' represents a halogen atom and $R_5$ represents a linear or branched alkyl radical having from 1 to 6 carbon atoms, an aryl radical or an aryl-$(C_1-C_4)$alkyl radical, the aryl radical being, for example, a phenyl radical, to obtain a compound of formula (VII):

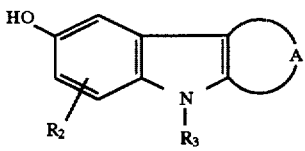

in which $R_2$, $R_3$ and A are as defined above, which compound of formula (VII) is reacted with a compound of formula (VIII):

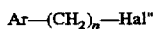

in which Ar and n are as defined in formula (I) and Hal" represents a halogen atom, to obtain, optionally after saponification to produce the carboxylated compound from the ester present in $R_3$, the compound of formula (I):

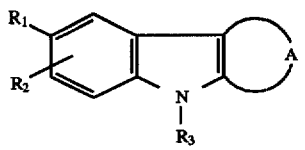

in which $R_1$, $R_2$, $R_3$ and A are as defined above, which compounds of formula (I) may optionally be:

purified by one or more methods selected from crystallisation, chromatography on a column of silica, extraction, filtration, and passage over charcoal or resin, separated, in pure form or in the form of a mixture, into their possible optical isomers, and converted into pharmaceutically acceptable salts with a base or an acid.

The invention relates also to a process for the preparation of compounds of formula (I) that is characterised in that the compound of formula (II'):

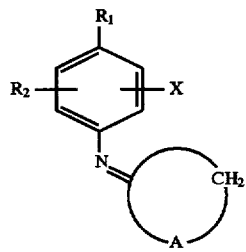

in which $R_1$, $R_2$ and A are as defined in formula (I) and X represents a halogen atom, is condensed in the presence of sodium amide or a combination thereof with an alcoholate (complex base), such as the complex base sodium amide-sodium tert.-butoxide ($NaNH_2$-tBuONa), to obtain:

either a compound of formula (III'):

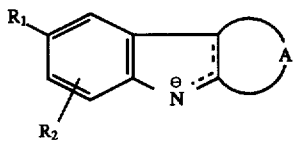

in which $R_1$, $R_2$ and A are as defined above, or, after hydrolysis, a compound of formula (I/a):

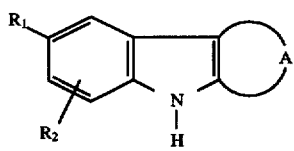

in which $R_1$, $R_2$ and A are as defined above, which compound of formula (III'), or compound of formula (I/a) in the form of its alkali salt, is substituted on the indole nitrogen by a radical of the formula $R_3'$, wherein $R_3'$ has the same meanings as $R_3$ in the definition of formula (I) with the exception of hydrogen, to obtain a compound of formula (I/b):

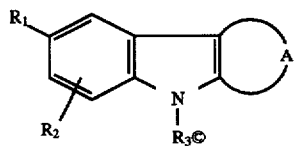

in which $R_1$, $R_2$, A and $R_3'$ are as defined above, which reaction is optionally followed by saponification to produce the carboxylated compound from the ester present in $R_3$, the compounds of formulae (I/a) and (I/b) forming the totality of the compounds of formula (I), which compounds of formula (I) may optionally be:

purified by one or more methods selected from crystallisation, chromatography on a column of silica, extraction, filtration, and passage over charcoal or resin, separated, in pure form or in the form of a mixture, into their possible optical isomers, and converted into pharmaceutically acceptable salts with a base or an acid.

The substitution of the compound of formula (III) or (IV) (or (III') or (I/a)) as defined above by a radical of the formula —$R_3'$, which substitution is provided in the above synthesis processes, can be carried out by reacting a compound of formula (III) or an alkali salt of formula (IV) (or (III') or (I/a), respectively) with a compound of the formula $R_3'$-X", Cl—COO—$R_3$", $(R_3—O)_2SO_2$, X—$(CH_2)_n$—$COOR_3$" or ($R_3$"—O—CO$)_2$O wherein $R_3'$ is as defined above, $R_3$" represents a $(C_1-C_6)$alkyl radical and X" represents a halogen atom, which reaction is optionally followed by a hydrolysis or saponification step in order to obtain the acid function from the ester, when $R_3$ represents an alkoxycarbonylalkyl radical.

For example, the invention relates to:

Preparation of the Complex Base:

To a suspension of 7 equivalents (eq.) of sodium amide (including 2 eq. for the preparation of the alcoholate and 1 eq. for the preparation of the imine or enamine enolate) in tetrahydrofuran (7 cm³ for 70 mmol of sodium amide) there are added dropwise 2 eq. of 2-methylpropan-2-ol at room temperature. After the addition, the mixture is heated at 45° C. for 2 hours (the ratio $NaNH_2$/t-BuONa is then 2/1 at the time of the cyclisation step).

Cyclisation of the Imines:

1 eq. of the imine to be condensed in solution in tetrahydrofuran (3 cm³ for 1 mmol) is added at 0° C. to the basic medium prepared above. The mixture is stirred magnetically at room temperature or 40°–45° C. The reaction is monitored by gas chromatography.

Preparation of (thia)cycloalkyl[b]indoles that are not Substituted on the Nitrogen (hydrolysis):

When all the starting material has disappeared, hydrolysis is carried out at 0° C. After extraction with ether, the organic phase is dried over magnesium sulfate and the solvents are evaporated off under reduced pressure. The (thia)cycloalkyl[b]indole is then purified by liquid chromatography.

N-methylation in Situ: Preparation of N-methylated (thia)cycloalkyl[b]indoles:

When all the starting material has disappeared, the reaction mixture is decanted and the liquid portion is subsequently transferred to a Mariotte flask and then added dropwise to 3 eq. of dimethyl sulfate in solution in tetrahydrofuran at 0° C. When the addition is complete, the reaction mixture is allowed to warm to room temperature. After 2 hours, the mixture is hydrolysed with a 32% aqueous ammonium hydroxide solution and then extracted with methylene chloride. The organic phase is subsequently washed with water and then dried over magnesium sulfate, and the solvents are evaporated off under reduced pressure. The N-methylated (thia)cycloalkyl[b]-indole is then purified by liquid chromatography.

N-carbethoxymethylation in Situ: Preparation of N-carbethoxymethylated (thia)cycloalkyl[b]indoles:

The liquid portion of the reaction mixture is transferred to an addition flask and added dropwise to a solution of ethyl bromoacetate (3 eq.) in dimethylformamide (6 cm³ for 1 mmol, at room temperature). After 2 hours, extraction is carried out with ether, the organic phase is washed with water and dried over magnesium sulfate, and the solvents are evaporated off under reduced pressure. The (thia)cycloalkyl[b]indole so obtained is then purified by liquid chromatography.

Saponification: Formation of N-(carboxymethyl)-(thia)cycloalkyl[b]indoles:

The N-(carbethoxymethyl)-(thia)cycloalkyl[b]indole prepared above is placed at reflux in a 10% solution of potassium hydroxide in ethanol. The reaction is monitored by thin-layer chromatography (TLC).

When all the starting material has disappeared, the reaction mixture is poured onto ice and extracted with ether. The aqueous phase is then acidified and again extracted with ether. The organic phase is dried over magnesium sulfate and the solvents are then evaporated off under reduced pressure. The N-(carboxymethyl)-(thia)cycloalkyl[b]indole is purified by liquid chromatography.

Demethylation: Formation of hydroxy(thia)cycloalkyl[b]indoles:

1.5 eq. of aluminium chloride are mixed with 20 eq. of phenylmethanethiol at 0° C. The (thia)cycloalkyl[b]indole (1 eq.) is added in solution in methylene chloride (5 cm³ for 1 mmol). After half an hour's reaction, an identical mixture of aluminium chloride/phenylmethanethiol is again added to the reaction mixture. The reaction is monitored by thin-layer chromatography. When all the starting material has disappeared, acid hydrolysis is carried out, followed by extraction with methylene chloride. The organic phase is dried over sodium sulfate and the solvents are then evaporated off under reduced pressure. The phenolic indole is isolated by liquid chromatography.

Formation of 5-benzyloxy(thia)cycloalkyl[b]indoles:

1.8 eq. of potassium carbonate, 3 eq. of phenylmethanethiol and 0.2 eq. of triethylbenzylammonium chloride are added at room temperature to 1 eq. of 5-hydroxyindole in solution in dimethylformamide (10 cm³ for 1 mmol). The reaction mixture is heated to 35°–40° C. When all the starting material has disappeared (monitored by TLC), the mixture is poured onto ice and extracted with dichloro-methane. The organic phase is dried over magnesium sulfate and the solvents are evaporated off under reduced pressure. The resulting 5-benzyloxy(thia)cycloalkyl[b]-indoles are purified by liquid chromatography.

Formation of 5-(2-quinolinoxymethyl)(thia)cycloalkyl[b]indoles:

The procedure is identical to that described above, but there are used 3.6 eq. of potassium carbonate, 1.5 eq. of 2-chloromethylquinoline hydrochloride and 0.4 eq. of triethylbenzylammonium chloride.

The compounds of formula (II) are readily accessible by reacting an aniline of formula (IIa):

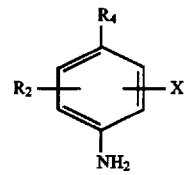
(IIa)

in which $R_2$ is as defined in formula (I), $R_4$ represents a linear or branched alkoxy radical having from 1 to 6 carbon atoms, and X represents a halogen atom, with a ketone of formula (IX):

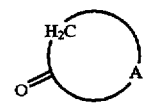
(IX)

in which A is as described in formula (I).

The compounds of formula (II') are readily accessible by reacting an aniline of formula (IIb):

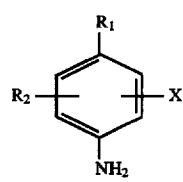
(IIb)

in which $R_1$ and $R_2$ are as defined in formula (I) and X represents a halogen atom, with a ketone of formula (IX):

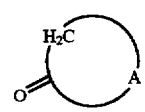
(IX)

in which A is as described in formula (I).

More especially, the imines can be prepared by subjecting 1 eq. of halogenamine and 1 eq. of ketone to azeotropic distillation in benzene. (The reaction may be catalysed by paratoluenesulfonic acid, zinc chloride, zinc bromide or the diethyl ether/boron trifluoride complex, as the case may be). When the appropriate amount of water has been recovered, the imine is distilled under reduced pressure.

The starting materials used in the above-described preparation processes are either commercially available or readily accessible to the person skilled in the art from the literature.

By virtue of their action, the compounds of the invention are, therefore, new clinical candidates for the treatment and prevention of inflammatory diseases and pathological inflammatory conditions.

The compounds of the invention are powerful lipoxygenase inhibitors (Pharmacological study: Example A) and possess an intense anti-inflammatory activity (Pharmacological study: Example B). Accordingly, the compounds of the invention can be used in the treatment and prevention of chronic or acute, articular, pulmonary, cutaneous or renal inflammation, and especially in the prevention and treatment of arthritis, rheumatoid polyarthritis, osteoarthrosis, psoriasis, allergic disorders, asthma, inflammatory diseases of the intestine, gastrointestinal ulcers, ischaemia, atherosclerosis, respiratory distress and septic shock.

The compounds of the present invention also have very considerable anti-oxidant properties. In particular, pharmacological studies have shown that the compounds possess a remarkable and specific protective activity with regard to lipid peroxidation and, especially, the peroxidation of low density lipoproteins (LDL).

The present invention relates also to pharmaceutical compositions containing a compound of formula (I) or a pharmaceutically acceptable addition salt thereof with an acid or a base, on its own or in combination with one or more inert, non-toxic excipients.

Of the pharmaceutical compositions according to the invention there may be mentioned more especially those which are suitable for oral, percutaneous, cutaneous, parenteral, nasal, rectal, perlingual, ocular or pulmonary administration, especially injectable or drinkable preparations, aerosols, ocular or nasal drops, tablets, film-coated tablets, dragées, gelatin capsules, capsules, creams, patches and suppositories.

The dosage varies according to the age, weight and sex of the patient, the mode of administration, the nature and severity of the disorder, and according to any associated treatment. The doses range from 0.5 mg to 2 g per day, especially from 0.5 mg to 100 mg per day, for example from 5 mg to 50 mg per day.

Preparation 1: N-cyclooctylidenyl-3-chloro-4-methoxyaniline

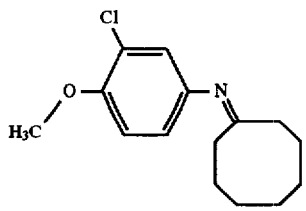

1 eq. of 3-chloroparaanisidine and 1 eq. of cyclooctanone are subjected to azeotropic distillation in toluene (100 cm³ for 50 mmol). The reaction is monitored by gas chromatography and is stopped after 48 hours. The imine is purified by distillation and is obtained in the form of a liquid in a yield of 68%.

¹H-NMR, δ (ppm): 6.2–6.9 (3H, m, H arom.); 3.8 (3H, s, MeO); 1.3–2.8 (14H, m, 7×CH₂)

I.R.: 2930–2857 (C—H); 1644 (N=C)

Preparation 2: N-cycloheptylidenyl-3-chloro-4-methoxyaniline

The title compound is obtained by azeotropic distillation from 3-chloro-4-methoxyaniline and cycloheptanone, using paratoluenesulfonic acid as catalyst and benzene as solvent.

The reaction is monitored by gas chromatography. When the reaction is complete, the mixture is brought back to room temperature, treated with a saturated sodium hydrogen carbonate solution, extracted with ether and dried over magnesium sulfate. The solvents are removed in vacuo. The imine is purified by distillation or is used as such.

Preparation 3: N-(thiopyranyliden-3-yl)-3-chloro-4-methoxyaniline 1 eq. of 3-chloroparaanisidine and 1 eq. of thiopyran-3-one are subjected to azeotropic distillation in benzene (100 cm³ for 50 mmol). The reaction is monitored by gas chromatography and is stopped after 5 hours. The imine is purified by distillation.
Yield: 40%
¹H-NMR, δ (ppm): 6.3–7.0 (3H, m, H arom.); 3.9 (3H, s, OMe); 3.3 (1H, s, C—H); 3.1 (1H, s, C—H); 2.0–3.0 (m, 6H, 3×CH₂)

EXAMPLE 1

ETHYL 2-(3-BENZYLOXY-5,6,7,8,9,10,11-HEPTAHYDRO CYCLOOCT[b]INDOL-11-YL) ACETATE

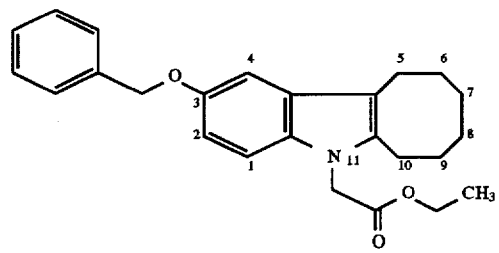

Step A:
3-methoxy-5,6,7,8,9,10,11-heptahydrocyclooct[b]indole

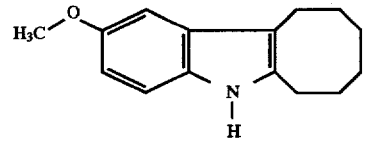

Preparation of the Complex Base:
To a suspension of 7 eq. of sodium amide in tetrahydrofuran (7 cm³ for 70 mmol of amide) there are added dropwise 2 eq. of 2-methylpropan-2-ol at room temperature. After the addition, the mixture is heated at 45° C. for 2 hours.

Condensation:
1 eq. of N-cyclooctylidenyl-3-chloro-4-methoxyaniline (preparation 1) in tetrahydrofuran (30 cm³ for 10 mmol) is added at 0° C. to the complex base prepared above. The mixture is stirred at room temperature for 24 hours. The reaction is monitored by gas chromatography. At the end of the reaction, the mixture is poured onto ice and extracted with ether. After drying over magnesium sulfate and evaporation of the solvents under reduced pressure, the indole is isolated by flash chromatography (eluant: ethyl acetate/ petroleum ether, 10:90).
Yield: 77%
Melting point: 102° C.
I.R.: 3405 (NH); 2922, 2848 (C—H)

Elemental analysis ($C_{15}H_{19}ON$ molecular weight: 229.32):

|  | C | H | N |
|---|---|---|---|
| % calculated | 78.56 | 8.35 | 6.10 |
| % found | 78.65 | 8.43 | 6.10 |

Step B: Ethyl 2-(3-methoxy-5,6,7,8,9,10,11-heptahydrocyclooct[b]indol-11-yl)acetate Procedure A:

The compound synthesised in step A is added at 0° C., in solution in dimethylformamide (5 cm³ for 1 mmol), to 1.2 eq. of sodium hydride. When the addition is complete, the reaction mixture is stirred at room temperature for 5 minutes. 2 eq. of ethyl bromoacetate are then added dropwise and the reaction mixture is stirred at room temperature. The reaction is monitored by thin-layer chromatography (TLC). When the reaction is complete, the reaction mixture is poured onto ice and extracted with methylene chloride. After drying over magnesium sulfate and evaporation of the solvents under reduced pressure, the title compound is isolated by flash chromatography (eluant: acetone/hexane, 10:90).
Yield: 72%
Melting point: 50° C.
I.R.: 2982, 2928, 2850 (C—H); 1753 (C=O)

Elemental analysis ($C_{19}H_{25}O_3N$ molecular weight: 315.41):

|  | C | H | N |
|---|---|---|---|
| % calculated | 72.35 | 7.98 | 4.44 |
| % found | 71.78 | 8.10 | 4.36 |

Procedure B:

At the end of the condensation carried out in step A, the reaction mixture is decanted under a stream of nitrogen. The supernatant is transferred, at room temperature, into a solution of 4 eq. of ethyl bromoacetate in dimethylformamide (so as to have a tetrahydrofuran/dimethylformamide mixture=½ at the end of the addition). When the reaction is complete (monitored by TLC), the procedure described above is followed (Procedure A).
Yield: 42%

Step C: Ethyl2-(3-hydroxy-5,6,7,8,9,10,11-heptahydrocyclooct[b]indol-11-yl)acetate 1 eq. of the compound obtained in step B in solution in dry methylene chloride (5 cm³ for 1 mmol) is added to a suspension of 1.5 eq. of aluminium chloride and 20 eq. of phenylmethanethiol at 0° C. The reaction mixture is stirred magnetically for ½ hour before a further 1.5 eq. of aluminium chloride and 20 eq. of phenylmethanethiol are added. The reaction mixture is stirred for a further 1.5 hours at 0° C. After acid hydrolysis at 0° C. (1N hydrochloric acid), extraction is carried out with methylene chloride, followed by washing with water and with a saturated sodium chloride solution. After drying over sodium sulfate and evaporation of the solvents, ethyl 2-(3-hydroxy-5,6,7,8,9,10,11-heptahydrocyclooct[b]indol-11-yl)acetate is isolated by flash chromatography (eluant: ethyl acetate/petroleum ether, 20:80).

Yield: 60%
Melting point: 100° C.
I.R.: 3406 (OH); 2980, 2927, 2850 (C—H); 1753 (C=O)

Elemental analysis ($C_{18}H_{23}O_3N$ molecular weight: 301.39):

|  | C | H | N |
|---|---|---|---|
| % calculated | 71.73 | 7.69 | 4.64 |
| % found | 71.49 | 7.67 | 4.77 |

Step D: Ethyl 2-(3-benzyloxy-5,6,7,8,9,10,11-heptahydrocyclooct[b]indol-11-yl)acetate 1.8 eq. of potassium carbonate, then 1.2 eq. of benzyl chloride and finally 0.2 eq. of triethylbenzylammonium chloride are added, at room temperature, to a solution of the compound obtained in step C in dimethylformamide (10 cm³ for 1 mmol). The reaction mixture is heated at 35°–40° C. for 5 hours and the reaction is monitored by TLC. When the reaction is complete, hydrolysis is carried out on ice, followed by extraction with methylene chloride. After washing with water, drying over magnesium sulfate and evaporation of the solvents under reduced pressure, the title compound is isolated by flash chromatography (eluant: ethyl acetate/ petroleum ether, 15:85).
Yield: 77%
Melting point: oil
I.R.: 2927, 2850 (C—H); 1753 (C=O)

Elemental analysis ($C_{25}H_{29}O_3N$ molecular weight: 391.51):

|  | C | H | N |
|---|---|---|---|
| % calculated | 76.69 | 7.46 | 3.57 |
| % found | 76.76 | 7.51 | 3.61 |

EXAMPLE 2

ETHYL 2-{3-[(QUINOL-2-YL)METHYLOXY]-5,6,7,8,9,10,11-HEPTAHYDROCYCLOOCT[b]INDOL-11-YL}ACETATE 1.8 eq. (×2) of potassium carbonate, 1.5 eq. of

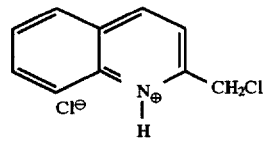

and finally 0.2 eq. (×2) of triethylbenzylammonium chloride are added, at room temperature, to a solution of the compound obtained in step C of Example 1 in dimethylformamide (10 cm³ for 1 mmol). The reaction mixture is heated at 40° C. for 20 hours and the reaction is monitored by TLC. When the reaction is complete, hydrolysis is carried out an ice, followed by extraction with methylene chloride. After washing with water, drying over magnesium sulfate and evaporation of the solvents under reduced pressure, the title compound is isolated by flash chromatography (eluant: ethyl acetate/petroleum ether, 15:85).
Yield: 86%
Melting point: 60° C.
I.R.: 2925, 2852 (C—H); 1753 (C=O)

EXAMPLE 3

2-(3-BENZYLOXY-5,6,7,8,9,10,11-HEPTAHYDROCYCLOOCT[b]INDOL-11-YL) ACETIC ACID

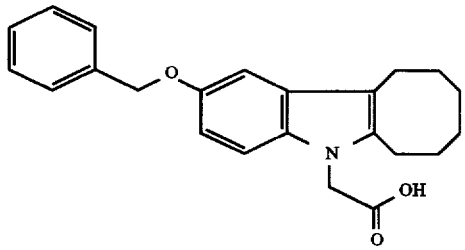

The compound obtained in Example 1 (step D) is placed in a 10% solution of potassium hydroxide in ethanol and is refluxed for 3 hours. The solution is extracted with ether and the aqueous phase is then acidified and again extracted with ether. After washing with water, drying over magnesium sulfate and evaporation of the solvents, the title compound is isolated by flash chromatography (eluant: ethyl acetate/petroleum ether, 50:50).

Yield: 65%
Melting point: 105° C.
I.R.: 3700 to 2200 (OH); 2923, 2849 (C—H); 1720 (C=O)

| Elemental analysis ($C_{23}H_{25}O_3N$ molecular weight: 399.49): | | | |
|---|---|---|---|
| | C | H | N |
| % calculated | 76.00 | 6.93 | 3.85 |
| % found | 75.99 | 7.23 | 3.94 |
| I.R.: 3600 to 2200 (OH); 1750 (C=O) | | | |
| Melting point (hydrochloride): 135° C. | | | |

EXAMPLE 4

2-{3-[(QUINOL-2-YL)METHYLOXY]-5,6,7,8,9,10,11-HEPTAHYDRO-CYCLOOCT[b]INDOLE}ACETIC ACID

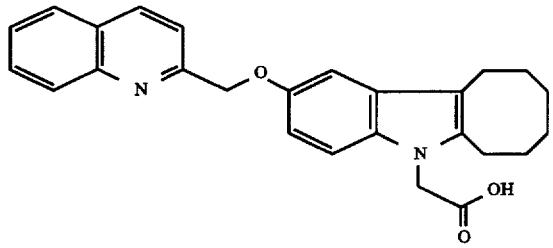

The title compound is obtained following the procedure of Example 3, but starting from the compound of Example 2.

Melting point (hydrochloride): 135° C.
I.R.: 3600 to 2200 (OH); 1750 (C=O)

EXAMPLE 5

ETHYL 2-(3-BENZYLOXY-5,6,7,8,9,10-HEXAHYDRO-CYCLOHEPT[b]INDOL-10-YL) ACETATE

Step A: 3-methoxy-5,6,7,8,9,10-hexahydrocyclohept[b]indole

Preparation of the Complex Base:

To a suspension of 7 eq. of sodium amide in tetrahydrofuran (7 cm³ for 70 mmol of sodium amide) there are added dropwise 2 eq. of 2-methylpropan-2-ol at room temperature. After the addition, the mixture is heated at 45° C. for 2 hours.

Condensation:

1 eq. of N-cycloheptylidenyl-3-chloro-4-methoxyaniline (preparation 2) is added, at 0° C., to the complex base prepared above. The mixture is stirred at room temperature until the reaction is complete. The reaction is monitored by gas chromatography. The 3-methoxy-5,6,7,8,9,10-hexahydrocyclohept[b]indole is separated by liquid chromatography.

Then, following the procedure of steps B to D of Example 1, but starting from the compound obtained in step A, the compounds of the following steps are obtained:

Step B: Ethyl 2-(3-methoxy-5,6,7,8,9,10-hexahydrocyclohept[b]indol-10-yl)acetate
Step C: Ethyl 2-(3-hydroxy-5,6,7,8,9,10-hexahydrocyclohept[b]indol-10-yl)acetate
Step D: Ethyl 2-(3-benzyloxy-5,6,7,8,9,10-hexahydrocyclohept[b]indol-10-yl) acetate

EXAMPLE 6

ETHYL 2-{3-[(QUINOL-2-YL)METHYLOXY]-5,6,7,8,9,10-HEXA HYDROCYCLOHEPT[b]INDOL-10-YL}ACETATE

Melting point: 66° C.

EXAMPLE 7

2-(3-BENZYLOXY-5,6,7,8,9,10-HEXAHYDROCYCLO-HEPT[b]INDOL-10-YL) ACETIC ACID

EXAMPLE 8

2-{3-[(QUINOL-2-YL)METHYLOXY]-5,6,7,8,9,10-HEXAHYDRO-CYCLOHEPT[b]INDOL-10-YL}ACETIC ACID

EXAMPLE 9

ETHYL 2-{8-[(QUINOL-2-YL)METHYLOXY]THIOPYRANO-[3,2-b]INDOL-5-YL}ACETATE

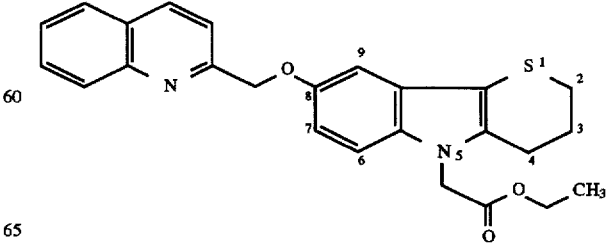

First Method

Step A: ethyl 2-(8-hydroxythiopyrano[3,2-b]indol-5-yl) acetate

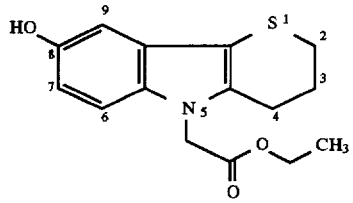

In refluxed toluene (100 ml for 50 mmol) am mixed 1 eq. of 3-chloro-4-(tetrahydropyran-2-yloxy)phenylamine and 1 eq. of dihydrothiopyran-3-one with 0.035 eq. of acetic acid. The reaction is monitored by gas chromatography. After 31 hours, the reaction mixture is neutralised with potassium carbonate. After filtering, drying over magnesium sulfate, the solvent is evaporated under reduced pressure. The so obtained imine in solution in tetrahydrofuran (30 ml for 10 mmol) is added at 0° C. to the complex base sodium amide/sodium tertio-butylate. The reaction is monitored by gas chromatography. At the end of the condensation (after 24 hours) the reaction mixture is decanted under a stream of nitrogen. The supernatant is transferred, at room temperature, into a solution of 4 eq. of ethyl bromoacetate in dimethylformamide (so as to have a THF/DMF mixture=½ at the end of the addition). When the reaction is complete (monitored by TLC), the methanol is evaporated. The obtained residue is diluted into ether and washed with a 5% solution of sodium hydrogenocarbonate. The organic phase is dried over magnesium sulfate. The solvent is evaporated under reduced pressure. The title compound is obtained in crude form and is then purified by flash chromatography (eluent: acetone/hexane, 20:80).

Yield: 25%

I.R. :3449 (OH); 1741 (C=O)

$^1$H-NMR, δ (ppm): 7.00–6.70 (m, 3H, H$_{arom.}$) ; 4.80 (s, 1H, OH); 4.70 (s, 2H, CH$_2$CO$_2$Et); 4.15 (q, 2H, CO$_2$CH$_2$CH$_3$); 3.00–2.20 (m, 6H, 3×CH$_2$); 1.20 (t, 3H, CO$_2$CH$_2$CH$_3$)

Step B: ethyl 2-{8-[(quinol-2-yl)methyloxy]thiopyrano-[3,2-b]indol-5-yl}acetate To a solution of 1 eq. of the compound obtained in the preceding step in dimethylformamide (10 ml for 1 mmol) are added, at room temperature, 2 eq. (×2) of potassium carbonate and then 1.5 eq. of 2-chloromethylquinoline chlorhydrate and finally 0.2 eq. (×2) of tetrabutylammonium hydrogenosulfate. The reaction mixture is heated at 40° C. during 27 hours. The reaction is monitored by TLC. When the starting product has disappeared, the reaction is poured onto ice and extracted with ether. After washing with water, drying over magnesium sulfate and evaporation of the solvents under reduced pressure, the title compound, obtained in crude form, is purified by flash chromatography (eluent: methanol/methylene chloride, 2:998).

Yield: 50[{]jf44aSecond Method

Step A: 8-methoxythiopyrano[3,2-b]indole

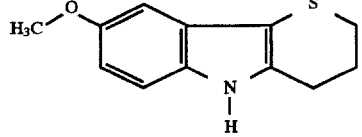

Preparation of the Complex Base:

To a suspension of 7 eq. of sodium amide in tetrahydrofuran (7 cm$^3$ for 70 mmol of sodium amide) there are added dropwise 2 eq. of 2-methylpropan-2-ol at room temperature. After the addition, the mixture is heated at 45° C. for 2 hours.

Condensation:

Procedure 1:

1 eq. of N-(thiopyranyliden-3-yl)-3-chloro-4-methoxyaniline (preparation 3) in solution in tetrahydrofuran (30 cm$^3$ for 10 mmol) is added at 0° C. to the complex base prepared above.

The mixture is stirred at room temperature for 12 hours. The reaction is monitored by gas chromatography. At the end of the reaction, the reaction mixture is poured onto ice and extracted with ether.

After drying over magnesium sulfate and evaporation of the solvents under reduced pressure, the title compound is isolated by flash chromatography (Kieselgel 40–63 mesh) (eluant: ethyl acetate/petroleum ether, 5:95).

Yield: 53%

Melting point: 123° C.

I.R.: 3390 (NH), 2999, 2938, 2922, 2834 (C—H)

| Elemental analysis (C$_{12}$H$_{13}$ONS molecular weight: 219.30): | | | | |
|---|---|---|---|---|
| | C | H | N | S |
| % calculated | 65.72 | 5.97 | 6.38 | 14.62 |
| % found | 65.95 | 6.03 | 6.53 | 14.93 |

Procedure 2:

The crude imine obtained in preparation 3 from 1 eq. of ketone and 1 eq. of amine is added at 0° C., without being purified, to the complex base prepared above. The reaction is carried out as for procedure 1.

Yield: 36.5%, based on the ketone.

Step B: Ethyl 2-(8-methoxythiopyrano[3,2-b]indol-5-yl) acetate

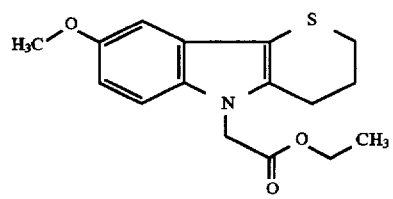

Procedure 1:

The crude reaction mixture obtained in the preceding step is decanted under a stream of nitrogen. The supernatant that is obtained is transferred into a solution of 4 eq. of ethyl bromoacetate in dimethylformamide (so as to have a THF/DMF mixture=½ at the end of the addition), at room temperature.

When the reaction is complete, the reaction mixture is poured onto ice and then extracted with ether. Customary treatment of the organic phase yields a crude compound which is purified by flash chromatography (eluant: acetone/hexane, 15:85).

Yield: 46%

Melting point: 98° C.

I.R.: 2923 (CH), 1750 (C=O)

Elemental analysis ($C_{16}H_{13}O_3NS$ molecular weight: 299.34):

|             | C     | H    | N    | S     |
|-------------|-------|------|------|-------|
| % calculated | 62.92 | 6.27 | 4.58 | 10.49 |
| % found      | 62.58 | 6.32 | 4.69 | 10.36 |

Procedure 2:

The indole obtained in step A, in solution in dimethylformamide (5 cm³ for 1 mmol), may also be added, at 0° C., to 1.2 eq. of sodium hydride. When the addition is complete, the reaction mixture is stirred at room temperature for 5 minutes. 2 eq. of ethyl bromoacetate are then added dropwise, and the reaction mixture is stirred at room temperature.

When the reaction is complete, the reaction mixture is poured onto ice and then extracted with ether. Customary treatment of the organic phase yields a crude compound which is purified by flash chromatography (eluant: acetone/hexane, 15:85).

Step C: Ethyl 2-(8-hydroxythiopyrano[3,2-b]indol-5-yl)acetate

Following the procedure of Step C of Example 1, the title compound is obtained.

Step D: Ethyl 2-{8-[(quinol-2-yl)methyloxy]thiopyrano[3,2-b]indol-5-yl}acetate

Following the procedure of Example 2, the title compound is obtained.

EXAMPLE 10

2-{8-[(QUINOL-2-YL)METHYLOXY]THIOPYRANO[3,2-b]INDOL-5-YL}ACETIC ACID

The compound obtained in Example 9 is placed in a 10% solution of potassium hydroxide in ethanol and is refluxed for 3 hours. The reaction mixture is extracted with ether and the aqueous phase is then acidified and again extracted with ether.

After customary treatment of the organic phase, the desired crude compound is purified by recrystallisation from dimethylformamide.

Melting point: 215° C.

I.R.: 3463 (OH), 1794 (C=O)

Elemental analysis ($C_{23}H_{20}O_3N_2S$ molecular weight: 404.48):

|             | C     | H    | N    | S    |
|-------------|-------|------|------|------|
| % calculated | 68.30 | 4.98 | 6.92 | 7.93 |
| % found      | 68.42 | 5.07 | 6.85 | 7.67 |

EXAMPLES 11 TO 26

Using the methods described above, but starting from the appropriate reagents, there are obtained the compounds of the following Examples, which are representative of the invention:

EXAMPLE 11

ETHYL 2-{3-[(THIAZOL-2-YL)METHYLOXY]-5,6,7,8,9,10,11-HEPTAHYDROCYCLOOCT[b]INDOL-11-YL}ACETATE

EXAMPLE 12

2-{3-[(THIAZOL-2-YL)METHYLOXY]-5,6,7,8,9,10,11-HEPTAHYDROCYCLOOCT[b]INDOL-11-YL}ACETIC ACID

EXAMPLE 13

ETHYL 2-{3-{[4-(PROP-2-YL)THIAZOL-2-YL]METHYLOXY}-5,6,7,8,9,10,11-HEPTAHYDROCYCLOOCT[b]INDOL-11-YL}ACETATE

EXAMPLE 14

ETHYL 2-{3-[(5-CHLOROOXAZOL-2-YL)METHYLOXY]-5,6,7,8,9,10,11-HEPTAHYDROCYCLOOCT[b]INDOL-11-YL}ACETATE

EXAMPLE 15

ETHYL 2-{3-[(1,2,5-THIADIAZOL-3-YL)METHYLOXY]-5,6,7,8,9,10,11-HEPTAHYDROCYCLOOCT[b]INDOL-11-YL}ACETATE

EXAMPLE 16

ETHYL 2-{3-[(THIAZOL-4-YL)METHYLOXY]-5,6,7,8,9,10,11-HEPTAHYDROCYCLOOCT[b]INDOL-11-YL}ACETATE

EXAMPLE 17

2-{3-[(THIAZOL-4-YL)METHYLOXY]-5,6,7,8,9,10,11-HEPTAHYDROCYCLOOCT[b]INDOL-11-YL}ACETIC ACID

EXAMPLE 18

ETHYL 2-{3-[(THIEN-2-YL)METHYLOXY]-5,6,7,8,9,10,11-HEPTA HYDROCYCLOOCT[b]INDOL-11-YL}ACETATE

EXAMPLE 19

ETHYL 2-{3-[(2-METHYLTHIAZOL-4-YL)METHYLOXY]-5,6,7,8,9,10,11-HEPTAHYDROCYCLOOCT[b]INDOL-11-YL}ACETATE

EXAMPLE 20

2-{3-[(2-METHYLTHIAZOL-4-YL)METHYLOXY]-5,6,7,8,9,10,11-HEPTAHYDROCYCLOOCT[b]INDOL-11-YL}ACETIC ACID

EXAMPLE 21

ETHYL 2-{3-[(6-CHLOROPYRID-2-YL)METHYLOXY]-5,6,7,8,9,10,11-HEPTAHYDROCYCLOOCT[b]INDOL-11-YL}ACETATE

EXAMPLE 22

ETHYL 2-{3-[(PYRID-3-YL)METHYLOXY]-5,6,7,8,9,10,11-HEPTAHYDROCYCLOOCT[b]INDOL-11-YL}ACETATE

EXAMPLE 23

ETHYL 2-{3-[(NAPHTH-2-YL)METHYLOXY]-5,6,7,8,9,10,11-HEPTAHYDROCYCLOOCT[b]INDOL-11-YL}ACETATE

EXAMPLE 24

ETHYL 2-{3-[(4,6-DIMETHYLPYRID-2-YL)METHYLOXY]-5,6,7,8,9,10,11-HEPTAHYDROCYCLOOCT[b]INDOL-11-YL}ACETATE

EXAMPLE 25

ETHYL 2-{3-[(THIAZOL-2-YL)METHYLOXY]-5,6,7,8,9,10-HEXAHYDROCYCLOHEPT[b]INDOL-10-YL}ACETATE

EXAMPLE 26

ETHYL 2-{3-[(4,6-DIMETHYLPYRID-2-YL)METHYLOXY]-5,6,7,8,9,10-HEXAHYDROCYCLOHEPT[b]INDOL-10-YL}ACETATE

Pharmacological Study

EXAMPLE A:

Study of the Interaction of Compounds of the Invention with the Lipoxygenase and Cyclo-Oxygenase Activities of Rabbit Granulocytes Aim of the Study The object of this study is to determine the effects of compounds of the invention on the lipoxygenase and cyclo-oxygenase activities of rabbit granulocytes stimulated in vitro by A 23187, by measuring the levels of $PGE_2$ and $LTB_4$ thus liberated by means of an enzyme immunoassay (EIA).

Equipment and Methods

Obtaining the Granulocytes

The granulocytes are isolated from rabbit blood collected from the main artery of the ear according to the method described by Trush et al. (1978).

They are suspended, at a density of $10^6$ cells/$cm^3$, in a phosphate buffer (mM): NaCl: 137; KCl: 2.68; $Na_2HPO_4$: 8.1; $KH_2PO_4$: 1.47; $CaCl_2$: 0.9; $MgCl_2$: 0.5

Stimulation of the Cells

The freshly obtained granulocytes are pre-incubated for a period of 15 minutes at 37° C. in the presence of the test products.

| Products used | |
|---|---|
| Kit EIA $LTB_4$ | Amersham ® |
| Kit TIA $PGE_2$ | Amersham ® |
| A 23187 | Sigma ® |
| NDGA | Sigma ® |
| indomethacine | Sigma ® |
| standard products | Sigma ® |

Analysis of the Results

The results are expressed as percentages of the positive control. The values are presented as the mean±s.e.m. of three measurements carried out on the same day, for the "screening" study, and of three measurements carried out on three different days for the $IC_{50}$ study.

The $IC_{50}$ values and the Hill number values (Hn) are determined by modelling using the Hill equation.

Results:

The compounds of the invention prove to be powerful inhibitors of the 5 lipoxygenase pathway. This action is selective and does not interfere with the cyclo-oxygenase pathway.

Thus, at $10^{-7}M$, the compounds of Examples 2, 3 and 6 inhibit the production of $LTB_4$ completely, without reducing that of $PGE_2$.

EXAMPLE B:

Study of Anti-Inflammatory Activity: in vivo Study

The anti-inflammatory potential of the compounds was determined using a model of acute inflammation induced by the subcutaneous injection of a colloidal suspension of carrageenin into the plantar surface of the rear paws of rats, in accordance with a technique based on the method of WINTER, RISLEY and NUSS, Proc. Soc. Exp. Biol. Med., 111, 554, (1962), and WINEGAR et al., J. Pharmacol. Exp. Ther., 166, 96, (1969).

The male WISTAR EOPS rats are allocated at random into groups of 10 and receive the test substances per os one hour after the injection of 0.15 $cm^3$ of a 1% suspension of carrageenin into the left rear paw. The inflammation is measured 5 hours later by weighing the paws, and the percentages of inflammation and of anti-inflammatory activity (AIA) are calculated.

Results:

It appears that the compounds of the invention, when administered orally in a dose of 10 mg/kg, bring about a very considerable reduction in the volume of the induced oedema.

EXAMPLE C:

Study of Acute Toxicity

The acute toxicity was assessed following oral administration of increasing doses (0.1–0.25–0.50–0.75–1 g/kg) of compounds of the invention to groups of three mice (20±2 grammes). The animals were observed at regular intervals during the first day and then daily for the two weeks following the treatment. It appears that the compounds of the invention are completely non-toxic. No death is observed after administration of a dose of 1 g/kg. No disorders are noted after administration of that dose.

EXAMPLE D:

Study of Compounds of the Invention in a Model of Acute Cutaneous Inflammation in Mice (phorbol 12-myristate-13-acetate test)

In the following test, the measurements were carried out on groups of five mice. The tests on the groups of control mice are carried out at the same time as those on the groups of mice which have received the test compounds.

5 μg of phorbol 12-myristate-13-acetate in 20 μl of an ethanol/water mixture (8:2) are applied to the front and rear surfaces of the right ears of the mice, 30 minutes after the application in a similar manner of the test compounds or of the vehicle (2×20 μl at 5-minute intervals in absolute alcohol). The swelling of the ear is measured 6 hours later with the aid of a Dyer micrometer. That measurement is used as the inflammation index.

The results obtained are shown in the Table below:

| Compound | IC$_{50}$ (μM) |
|---|---|
| Example 2 | 20 |
| Example 3 | 170 |
| Example 4 | 15 |
| Example 6 | 10 |

EXAMPLE E:

Pharmaceutical Composition: Tablets

Preparation formula for 1000 tablets each containing a dose of 50 mg.

| | |
|---|---|
| ethyl 2-{3-[(quinol-2-yl)methoxy]-5,6,7,8,9,10,11-heptahydrocyclooct-[b]indol-11-yl}acetate | 50 g |
| wheat starch | 15 g |
| corn starch | 15 g |
| lactose | 65 g |
| magnesium stearate | 2 g |
| silica | 1 g |
| hydroxypropylcellulose | 2 g |

We claim:

1. A compound selected those of formula (I):

in which:

R$_1$ represents Ar—(CH$_2$)$_n$—O— wherein n represents zero or 1 to 4 inclusive and Ar is selected pyridyl, quinolyl, isoquinolyl, Ar being unsubstituted or substituted by one or more radicals selected from halogen, alkyl, alkoxy, hydroxy and trifluoromethyl;

R$_3$ is selected from carboxyalkyl and alkoxycarbonylalkyl; and

A represents —(CH2)m— wherein m is 3–6 inclusive, or represents a group of formula (α):

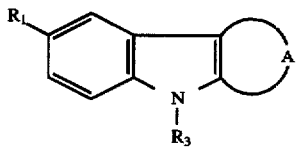

in which p is 1–4 inclusive;

wherein the terms "alkyl" and "alkoxy" denote linear or branched groups having 1 to 6 carbon atoms inclusive, their optical isomers, in pure form or in the form of a mixture, and their pharmaceutically-acceptable addition salts with an acid or a base.

2. A compound according to claim 1 in which A represents pentamethylene, its optical isomers, in pure form or in the form of a mixture, and its pharmaceutically-acceptable addition salts with an acid or a base.

3. A compound according to claim 1 in which A represents hexamethylene, its optical isomers, in pure form or in the form of a mixture, and its pharmaceutically-acceptable addition salts with an acid or a base.

4. A compound according to claim 1 in which A represents a group of formula:

its optical isomers, in pure form or in the form of a mixture, and its pharmaceutically-acceptable addition salts with an acid or a base.

5. A compound according to claim 1 in which Ar represents quinolyl, its optical isomers, in pure form or in the form of a mixture, and its pharmaceutically-acceptable addition salts with a base.

6. A compound according to claim 1 in which R$_3$ represents a radical selected from carboxyalkyl and alkoxycarbonylalkyl, its optical isomers, in pure form or in the form of a mixture, and its pharmaceutically-acceptable addition salts with an acid or a base.

7. A compound according to claim 1 which is 2-{8-[(quinol-2-yl)methyloxy]thiopyrano[3,2-b]indol-5-yl}acetic acid, or a pharmaceutically-acceptable addition salt thereof with an acid or a base.

8. A compound according to claim 1 which is ethyl 2-{3-[(quinol-2-yl)methyl-oxy]-5,6,7,8,9,10,11-heptahydrocyclooct[b]indol-11-yl}acetate.

9. A compound according to claim 1 which is ethyl 2-{3-[(quinol-2-yl)methyloxy]-5,6,7,8,9,10,-hexahydrocyclohept[b]indol-10-yl}acetate.

10. A method for treating a mammal afflicted with a disease requiring an anti-inflammatory agent comprising the step of administering to said mammal an amount of a compound of claim 1 which is effective for alleviation of said disease.

11. A pharmaceutical composition useful as an anti-inflammatory agent comprising an effective anti-inflammatory amount of a compound as claimed in claim 1 together with a pharmaceutically-acceptable excipient.

UNITED STATES PATENT AND TRADEMARK OFFICE
CERTIFICATE OF CORRECTION

PATENT NO. : 5,635,516
DATED : June 3, 1997
INVENTOR(S) : Paul Caubere et al.

It is certified that error appears in the above-indentified patent and that said Letters Patent is hereby corrected as shown below:

Column 2, line 60: In the drawing, delete "$R_3$ " with the copyright symbol beside it and replace it with -- $R_3'$ -- only.

Column 4, line 54: "$R_3-O)_2$" should read -- $(R_3'-O)_2$ --.

Column 5, line 19: "Situ" should read -- situ --.

Column 9, line 44: "supematant" should read -- supernatant --.

Column 13, line 21: "tetrahydrefuran" should read -- tetrahydrofuran --.

Column 13, line 58: Delete "[{]jf44aSecond Method" after the number 50 and replace by -- % --.

UNITED STATES PATENT AND TRADEMARK OFFICE
CERTIFICATE OF CORRECTION

PATENT NO. : 5,635,516
DATED : June 16, 1997
INVENTOR(S) : Paul Caubere et al.

It is certified that error appears in the above-indentified patent and that said Letters Patent is hereby corrected as shown below:

Column 13, line 59:  Insert new paragraph with this heading -- Second Method --.

Signed and Sealed this

Thirtieth Day of September, 1997

Attest:

BRUCE LEHMAN

Attesting Officer

Commissioner of Patents and Trademarks